Figure 1:
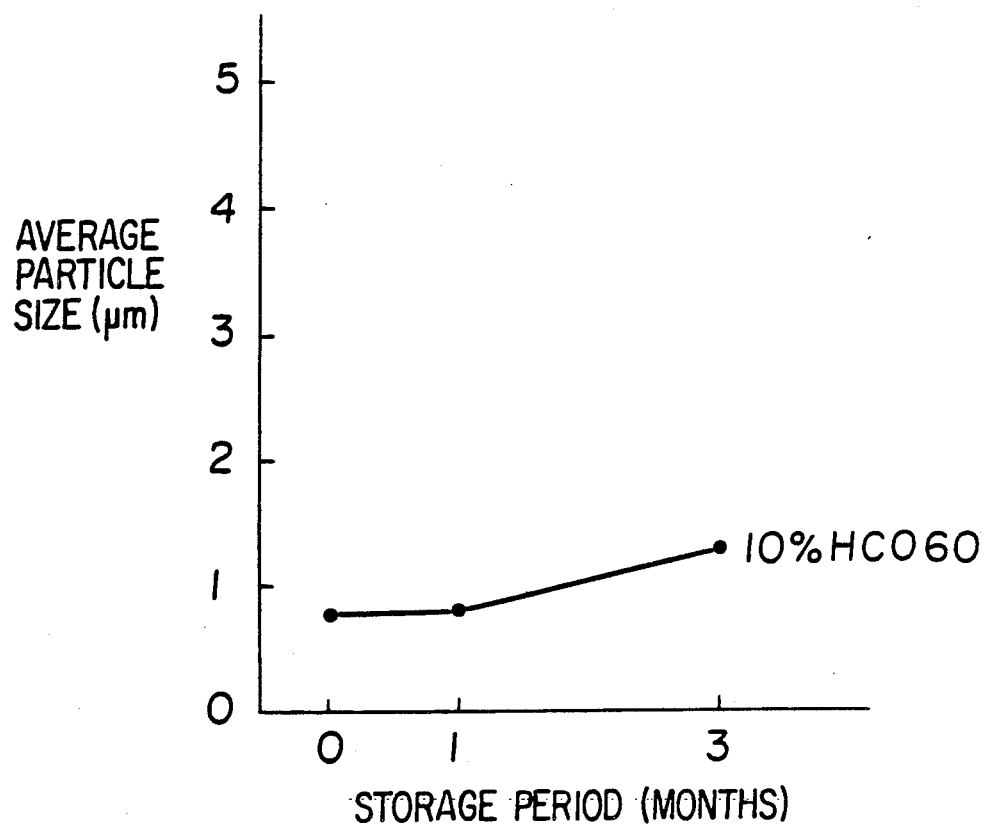

United States Patent [19]

Kondo et al.

[11] Patent Number: 5,002,952
[45] Date of Patent: Mar. 26, 1991

[54] READILY ABSORBED PHARMACEUTICAL COMPOSITION

[75] Inventors: Nobuo Kondo, Daito; Tsunetaka Nakajima, Kashiwara; Masahiro Watanabe, Akashi; Kazumasa Yokoyama, Toyonaka; Takahiro Haga, Shiga; Nobutoshi Yamada, Shiga; Hideo Sugi, Shiga; Toru Koyanagi, Kyoto, all of Japan

[73] Assignees: Ishihara Sangyo Kaisha Ltd.; The Green Cross Corporation, both of Osaka, Japan

[21] Appl. No.: 385,998

[22] Filed: Jul. 27, 1989

Related U.S. Application Data

[63] Continuation of Ser. No. 12,280, Feb. 9, 1987, abandoned.

[30] Foreign Application Priority Data

Feb. 8, 1986 [JP] Japan .................................. 61-26589

[51] Int. Cl.$^5$ .................. A61K 31/505; A61K 47/00; B01F 3/00
[52] U.S. Cl. .................................... 514/274; 514/785; 514/941; 514/975; 252/363.5
[58] Field of Search ............... 514/274, 785, 941, 975; 252/363.5

[56] References Cited

U.S. PATENT DOCUMENTS

| | | | |
|---|---|---|---|
| 4,677,110 | 6/1987 | Haga et al. | 514/274 |
| 4,677,111 | 6/1987 | Haga et al. | 514/274 |
| 4,727,077 | 2/1988 | Haga et al. | 514/274 |
| 4,849,425 | 7/1989 | Kondo et al. | 514/274 |
| 4,863,924 | 9/1989 | Haga et al. | 514/274 |

FOREIGN PATENT DOCUMENTS

| | | |
|---|---|---|
| 0025363 | 3/1981 | European Pat. Off. . |
| 107214 | 5/1984 | European Pat. Off. . |
| 0178572 | 4/1986 | European Pat. Off. . |
| 00192263 | 8/1986 | European Pat. Off. . |

OTHER PUBLICATIONS

Sangyo, Chem. Abst. 98(13):101190r (1983).
*Remington's Pharmaceutical Sciences*, 15th Ed., 1975, p. 296 and 335–337.
Dr. W. A. Ritschel, DIE TABLETTE, 1966, pp. 117–119.
Kirk–Othmer, Encyclopedia of Chemical Technology, 3rd Ed., vol. 5, 1980, p. 9.
Kirk–Othmer, Encyclopedia of Chemical Technology, 3rd Ed., vol. 9, 1980, p. 465.

*Primary Examiner*—Stanley J. Friedman
*Assistant Examiner*—Kevin E. Weddington
*Attorney, Agent, or Firm*—Oblon, Spivak, McClelland, Maier & Neustadt

[57] ABSTRACT

A pharmaceutical composition comprising a benzoyl urea compound having the formula:

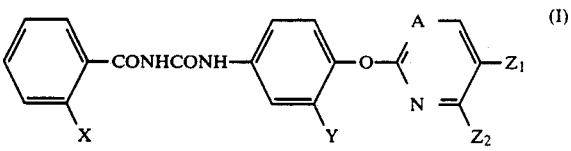

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is a =CH—group or a nitrogen atom, and a nonionic surfactant.

13 Claims, 1 Drawing Sheet

READILY ABSORBED PHARMACEUTICAL COMPOSITION

This application is a continuation of application Ser. No. 07/012,280, filed on Feb. 9, 1987, now abandoned.

The present invention relates to an antitumour pharmaceutical composition containing a benzoyl urea compound as the main component. More particularly, the present invention relates to a pharmaceutical composition whereby the absorbability of an antitumour benzoyl urea compound of the formula:

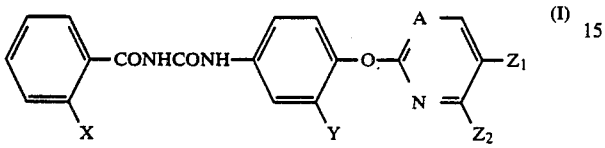

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is a =CH— group or a nitrogen atom, through the gut, is improved.

The benzoyl urea compounds of the formula I are known to have excellent antitumor activities (Japanese Unexamined Patent Publication No. 109721/1982). However, these compounds are hardly soluble in water, and accordingly their absorbability through e.g. the gut is poor. Therefore, in order to obtain adequate antitumour activities, it is necessary to increase the dose, whereby there is a possible danger of adverse effects due to the excessive administration.

It is an object of the present invention to provide a pharmaceutical composition whereby the absorbability of the benzoyl urea compound of the formula I through the gut is improved.

The present inventors have studied various additives with an aim to improve the absorbability of the benzoyl urea compound of the formula I through the gut, and have finally found that certain specific substances, i.e. nonionic surfactants, are capable of improving the absorbability of the benzoyl urea compound of the formula I through the gut.

Thus, the present invention provides a pharmaceutical composition comprising a benzoyl urea compound of the formula I and a nonionic surfactant.

Now, the present invention will be described in detail with reference to the preferred embodiments.

In the accompanying drawing, FIG. 1 is a graph showing the stability of particles of the pharmaceutical composition of the present invention.

In this specification, the halogen atom is preferably a chlorine atom or a bromine atom.

The following compounds may be mentioned as typical examples of the benzoyl urea compound of the formula I.

Compound No. 1: (Melting point: 182–185° C.)

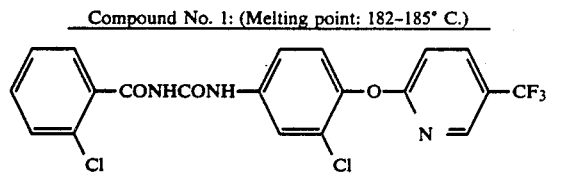

Compound No. 2: (Melting point: 235–238° C.)

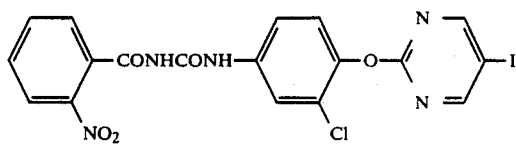

Compound No. 3: (Melting point: 229–231° C.)

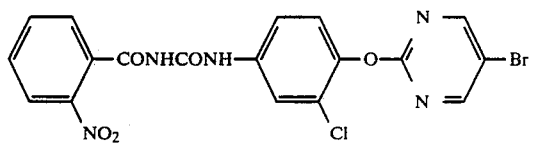

Compound No. 4: (Melting point: 207–208° C.)

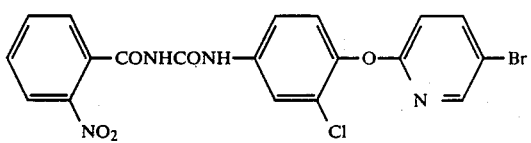

The benzoyl urea compounds of the formula I are known compounds, and they may be prepared by a method disclosed in e.g. Japanese Unexamined Patent Publication No. 109721/1982 or by a similar method.

There is no particular restriction as to the nonionic surfactant to be used in the present invention. Any nonionic surfactant may be employed so long as it is useful as an additive for pharmaceuticals. Its HLB value (Hydrophile-Lipophile Balance) is preferably at least 3. Specific Examples of such nonionic surfactants include polyoxyethylene hardened caster oil 20, polyoxyethylene hardened caster oil 40, polyoxyethylene hardened caster oil 60, polyoxyethylene hardened caster oil 100, polysorbate 60, polysorbate 65, polysorbate 80, polyoxyethylene polyoxypropylene glycol, a sucrose fatty acid ester, a glycerol fatty acid ester, a sorbitan fatty acid ester, a propylene fatty acid ester, a polyoxyethylene sorbitan fatty acid ester, a polyoxyethylene sorbitol fatty acid ester, a polyoxyethylene glycerol fatty acid ester, and a polyethylene glycol fatty acid ester.

In the present invention, the ratio of the benzoyl urea compound of the formula I to the nonionic surfactant is usually within a range of from 1:5 to 70:1 by weight.

The pharmaceutical composition of the present invention is preferably in the form of fine particles having an average particle size of from 0.2 to 1.0 μm.

The pharmaceutical composition of the present invention is preferably the one obtained by pulverizing the benzoyl urea compound of the formula I in an aqueous solution containing the nonionic surfactant, whereby the composition having the above-mentioned particle size will be prepared. In such a case, the nonionic surfactant serves as a dispersant. The pulverization is preferably conducted by wet pulverization. The wet pulverization is a method wherein the material to be pulverized is rotated or shaked together with beads (particularly glass beads) in a solution containing the dispersant. A machine such as a Dyno-Mile (KDL-model, manufactured by Dyno-Mile Company) may be employed for this purpose. The concentration of the benzoyl urea compound of the formula I in the aqueous solution during the pulverization, is from 1 to 70 w/v%, preferably from 20 to 50 w/v%. Particularly when the pulverization is conducted in a wet pulverization system by using the Dyno-mile, the concentration of the benzoyl urea compound of the formula I in the aqueous solution is preferably within the above range. The concentration of the nonionic surfactant as the dispersant is usually from 1 to 30 w/v%, preferably from 2 to 20 w/v%. The glass beads employed usually have a size of from 0.1 to 1.5 mm in diameter, preferably from 0.25 to 0.5 mm in diameter. The pulverization time is usually from 5 minutes to 1 hour. After the completion of the wet pulverization, glass beads will be removed by sieving, and if necessary additives such as a sweetening agent or a perfume may be added thereto. The composition is then subjected to autoclave sterilization or to filtration for the removal of bacteria, to obtain a liquid composition.

The composition of the present invention can be formulated into pharmaceutical formulations by conventional methods. As such pharmaceutical formulations, oral formulations such as powders, fine particles, granules, capsules, tablets and liquid drugs may be mentioned.

Such formulations may be prepared by removing water from the above-mentioned liquid composition by heat drying, freeze drying, centrifugal separation, membrane filtration, etc., and then following a conventional method for formulation by using or without using conventional pharmaceutical additives.

The pharmaceutical composition of the present invention may usually orally be administered to mammals (e.g. human beings, horses, cattles, dogs, mice, rats, etc.). The dose varies depending upon the diseased condition, the sex, the body weight, the formulation, etc. However, for instance, when the composition of the present invention is orally administered against human malignant lymphoma or lung cancer, the benzoyl urea compound of the formula I is administered in a daily dose of from 5 to 100mg/kg to an adult in one to three times per week.

As will be evident from Test Example 1, with the pharmaceutical composition of the present invention, the absorption of the benzoyl urea compound of the formula I from the gut is remarkably improved, and as will be shown from Test Example 2, the stability of the particles in a liquid state is good.

By using the pharmaceutical composition of the present invention, it is possible to reduce the dose of the benzoyl urea compound of the formula I and thus to reduce the side effects or the pain to the patient when it is administered.

Now, the present invention will be described with reference to Examples and Test Examples. However, it should be understood that the present invention is by no means restricted to these specific Examples.

TEST EXAMPLE 1:

Absorption from the gut

Compound No. 3 was suspended in each dispersing solvent containing a dispersant as identified below, so that the concentration will be 4 w/v%, and after an addition of glass beads (1–1.4 mm in diameter) in an amount of the same volume, subjected to rotary pulverization by a Dyno-mill for 45 minutes. As the dispersant, polyoxyethylene hardened caster oil 60 (HCO60, manufactured by Nikko Chemical K.K.), polyoxyethylene (160) polyoxypropylene (30) glycol (F68, manufactured by Asahi Denka Kogyo K.K.), a decaglycelin fatty acid ester (Decagly. ester, manufactured by Nikko Chemical K.K.), polysorbate 80 (Tween 80, manufactured by Nakarai Kagaku K.K.) and sucrose fatty acid ester (P1570, Sugar ester, manufactured by Hishito K.K.) were employed.

Each wet pulverized formulation thus obtained was forcibly orally administered by an oral sonde to a group of two Wister male rats (body weight: 200 g) starved for 18 hours (dose: 200 mg/5 ml/kg). Then, blood (0.3 ml) was periodically sampled with heparin from the jugular vein.

The blood thus obtained was subjected to separation of the plasma and removal of proteins by using acetonitrile, and then Compound No. 3 was quantitatively analyzed by a high speed liquid chromatography using a reversed phase column (Nova Pak $C_{18}$, 5 $\mu$, 3.9 mm in diameter $\times$ 150 mm, Nihon Waters), and the curve of the concentration in blood was prepared.

From the curve of the concentration in blood, the area below the curve was obtained by using a trapezoid formula and presented as AUC (Area Under the Curve). The respective values were obtained for all rats, and the average value and the width is shown in Table 1.

AUC is the highest with HCO60, and F68 follows it.

TABLE 1

| Dispersant | AUC (0–24 hr.) (mcg/ml.hr) |
|---|---|
| 10 w/v % HCO60 | 30.67 ± 0.21 |
| 10 w/v % F68 | 26.10 ± 0.51 |
| 10 w/v % Decagly.ester | 25.16 ± 1.12 |
| 10 w/v % Tween 80 | 24.72 ± 0.39 |
| 10 w/v % Sugar ester | 17.44 ± 0.21 |

TEST EXAMPLE 2:

Stability of particles

Among the wet pulverized formulations prepared in Test Example 1, the one wherein HCO60 was used as a dispersant, was subjected to a storage test at room temperature to examine the stability of particles in a liquid state. The change with time of the particle size (up to 3 months) is shown in FIG. 1. With HCO60, the increase in the particle size was little and the particles were stable.

TEST EXAMPLE 3:

Antitumour activities

The pharmacological effects of the pharmaceutical compositions obtained by the present invention were studied.

To $BDF_1$ mice (male, 20–22 g), L-1210 leukemia cells were intraperitoneally inoculated in an amount of $1 \times 10^6$ cells/mouse. One day later and 4 days later, a test drug was orally administered. It was difficult to administer the drug in the final formulation form. Therefore, in this test, Compound No. 3, and a 10 w/v% HCO60 solution were mixed, and pulverized in a wet system to obtain a liquid suspension, and the liquid suspension was administered to each mouse in an amount of 0.5 ml. Thereafter, the mice were observed for survival or death.

The activity was evaluated by a survival rate [T/C (%)]as compared with a control group to which a physiological saline was administered, and T/C values are shown in Table 2.

$$T/C\,(\%) = \frac{\text{Median survival time of test animals}}{\text{Median survival time of control animals}} \times 100$$

As the results, the adequate antitumour activity of Compound No. 3 was distinctly observed when it was subjected to wet pulverization together with the specific substance prescribed by the present invention, and no substantial antitumour activity was observed when Compound No. 3 was wet pulverized in the absence of HCO60 even when the compound was administered in the sam dose. Namely, this result indicates that the absorption i.e. the transfer of Compound No. 3 into blood from the gut, is facilitated by the composition of the present invention. On the other hand, the appearance of toxicity (T/C being less than 100%) in a high dose region indicates that the absorption is great.

This test result indicates that the adequate antitumour activity of Compound No. 3 is observed only in the case of the pharmaceutical composition of the present invention, and the activity is particularly remarkable in the composition obtained by wet pulverization. In particular, when HCO60 is used as a dispersant, the absorption is good over a wide range, thus indicating the possibility of an ideal drug when the clinical application is taken into account.

TABLE 2

| Administered formulation | T/C (%) |
|---|---|
| HCO60 + Compound No. 3 (Wet pulverized drug) | |
| Dose of Compound No. 3 (mg/kg) | |
| 400 | 32 |
| 200 | 128 |
| 100 | 224 |
| 50 | 200 |
| 25 | 178 |
| 12.5 | 128 |
| 6.25 | 92 |
| HCO60 + Compound No. 3 (Mixed drug) | |
| Dose of Compound No. 3 (mg/kg) | |
| 400 | 125 |
| 200 | 117 |
| HCO60 + Compound No. 3 (Wet pulverized drug) | |
| Dose of Compound No. 3 (mg/kg) | |
| 400 | 109 |
| 200 | 99 |
| CHO60 alone | 107 |
| Physiological saline (control) | 100 |

EXAMPLE 1

Compound No. 3 (5 g) was suspended in 50 ml of a 10 w/v% HCO60 aqueous solution, and the suspension was wet pulverized by a Dyno-mill by using 50 g of glass beads (1-1.5 mm in diameter). After the completion of pulverization, glass beads were removed by sieving, to obtain a wet pulverized drug of Compound No. 3.

The wet pulverized drug thus obtained was sterilized in an autoclave to obtain a liquid drug of a final form. Here, instead of the sterilization in an autoclave, it is possible to employ filtration to remove bacteria. If necessary, a sweetening agent, a perfume, etc. may be added.

EXAMPLE 2

To 40 ml of the liquid drug obtained in Example 1, 20 g of lactose was added. The mixture was freezed with dry ice-methanol, and then subjected to vacuum drying for 24 hours to remove water. The solid thus obtained was filled in capsules to obtain capsule drugs.

We claim:

1. A pharmaceutical composition comprising a benzoyl urea compound having the formula:

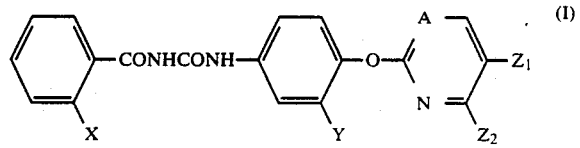

wherein X is a halogen atom or a nitro group, Y is a hydrogen atom or a halogen atom, $Z_1$ is a halogen atom, $Z_2$ is a hydrogen atom and A is a nitrogen atom, and a nonionic surfactant selected from the group consisting of polyoxyethylene castor oil 60, polyoxyethylene polyoxypropylene glycol, decaglycelin fatty acid ester, polysorbate 80 and sucrose fatty acid ester, wherein the ratio of the benzoyl urea compound of the formula I to the nonionic surfactant is within a range of from 1:5 to 70:1 by weight.

2. The pharmaceutical composition according to claim 1, wherein the benzoyl urea compound of the formula I is pulverized in an aqueous solution of a nonionic surfactant.

3. The pharmaceutical composition according to claim 1, wherein the composition is prepared by pulverizing the benzoyl urea compound of the formula I in an aqueous solution containing the nonionic surfactant, and then removing water from the liquid composition.

4. The pharmaceutical composition according to claim 1, which is in the form of fine particles having an average particle size of from 0.2 to 10 μm.

5. The pharmaceutical composition according to claim 1, wherein the nonionic surfactant has a hydrophile-lipophile balance of at least 3.

6. The pharmaceutical composition according to claim 1, wherein the nonionic surfactant is polyoxyethylene castor oil 60.

7. The pharmaceutical composition according to claim 1, wherein Y of the benzoyl urea compound (I) is a halogen atom.

8. The pharmaceutical composition according to claim 7, wherein Y is chloro.

9. The pharmaceutical composition according to claim 7, wherein the benzoyl urea compound is N-(2-nitrobenzoyl)-N'[3chloro-4(5-halogeno-2-pyrimidinyloxy) phenyl]urea 10. The pharmaceutical composition according to claim 9, wherein the benzoyl urea compound is N-(2-nitrobenzoyl)-N'-[3-chloro-4(5-bromo-2-pyrimidinyloxy) phenyl]urea.

11. The pharmaceutical composition according to claim 2, wherein the concentration of the benzoyl urea compound is from 1 to 70 w/v% and that of the nonionic surfactant is 1 to 30 w/v%.

12. The pharmaceutical composition according to claim 11, wherein the concentration of the benzoyl urea compound is from 20 to 500 w/v% and that of the nonionic surfactant is 2 to 200 w/v%.

13. The pharmaceutical composition according to claim 2, wherein the pulverization is conducted by using a Dyno-mile and employing glass beads having a size of from 0.1 to 1.5 mm in diameter, and the pulverization time is from 5 minutes to 1 hour.

* * * * *